United States Patent [19]

Hanlon et al.

[11] Patent Number: 4,679,567
[45] Date of Patent: Jul. 14, 1987

[54] PRESSURE TRANSDUCER

[75] Inventors: Stephen P. Hanlon; Walter L. Kerby, both of Sandy; Edmund R. Purdy, Fruitheights; James Strom, Salt Lake City, all of Utah

[73] Assignee: Deseret Medical, Inc., Sandy, Utah

[21] Appl. No.: 826,056

[22] Filed: Feb. 4, 1986

[51] Int. Cl.⁴ ............................................. A61B 5/02
[52] U.S. Cl. .................................. 128/675; 128/748; 73/708
[58] Field of Search ................. 128/672–673, 128/675, 748; 73/708, 715, 720, 740

[56] References Cited

U.S. PATENT DOCUMENTS

| | | | |
|---|---|---|---|
| 3,418,853 | 12/1968 | Curtis | 128/675 X |
| 4,274,423 | 6/1981 | Mizuno et al. | 128/675 |
| 4,465,075 | 8/1984 | Swartz | 128/672 |
| 4,539,998 | 9/1985 | McCord et al. | 128/675 |
| 4,557,269 | 12/1985 | Reynolds et al. | 128/675 |
| 4,576,181 | 3/1986 | Wallace et al. | 128/675 |
| 4,589,287 | 5/1986 | Dickens | 128/675 X |

FOREIGN PATENT DOCUMENTS 0079086  5/1983  European Pat. Off. ............ 128/748

OTHER PUBLICATIONS

Delannois; "Low-Cost IC Transducer for Med. Press. Measurements", Med. and Biol. Engr., vol. 12, No. 3, 5-1974, pp. 364–365.

Primary Examiner—Kyle L. Howell
Assistant Examiner—Angela D. Sykes
Attorney, Agent, or Firm—Aaron Passman

[57] ABSTRACT

Physiologic pressure transducers convert an applied pressure (e.g., blood pressure) into an electric signal, which can be displayed by a monitor as a numerical value or continuous waveform. While reusable pressure transducers have been used for a number of years, innovations in solid-state technology have made disposable transducers feasible. In particular, disposal transducers which are impedance matched for use with monitors formally used for reusable transducers are disclosed. The pressure transducer is rugged due to the careful mounting of the transducer diaphragm and integral compensation circuitry. In addition, the geometric configuration of the flow path is uniform such that debubbling of the unit is easy.

15 Claims, 2 Drawing Figures

PRESSURE TRANSDUCER

BACKGROUND OF THE INVENTION

An electrocardiogram (ECG) monitors the electrical activity of the heart, but the presence of an ECG signal does not indicate how effectively the blood is pumped through the arteries. Direct vessel blood pressure measurements are more accurate and reliable indicators of the state of the circulatory system. Accurate and continuous measurement of arterial and venous blood pressures can be obtained by placement of a catheter directly into the circulatory system. The vascular pressure can then be transmitted through fluid (usually saline) which is placed in the catheter attached to a pressure transducer.

Arterial blood pressure pulsates between peak (systolic) and minimum (diastolic) pressures. For a healthy young adult, these pressures are typically about 120 and 80 mm Hg, respectively, usually expressed as systolic over diastolic, or 120/80. Such arterial blood pressure monitoring may be necessary when an accurate assessment of the state of the circulatory system is required (e.g., during surgical procedures, following myocardial infarction, etc.). Similarly, continuous arterial pressure monitoring is used to estimate vital organ perfusion, to manage and monitor therapy, and to follow a patient's response to treatment during a hypertensive crisis.

The arterial pressure waveform often provides useful information on the pumping action of the heart and aortic valve closure. Observing the left radial arterial waveform is standard procedure when positioning intra-aortic balloon pumps to assist circulation, e.g., the pressure waveform gives early knowledge of mechanical problems with the monitoring line such as a clotted catheter.

Central venous pressure (CVP) is usually measured in the superior vena cava and typically ranges from 3 to 9 mm Hg above atmospheric pressure. A partial vacuum (below atmospheric pressure) of a few mm Hg can be created intermittently by respiratory efforts. CVP is monitored when fluids are being lost (e.g., in burn victims or patients undergoing major surgery) or gained (e.g., in patients receiving large infusions of blood or other fluids) because of its relationship to vascular fluid volume. Low CVP is a factor which can indicate hypovolemia (inadequate blood volume) due to hemorrhage or dehydration, and can precede or accompany shock. Excessively high CVP may accompany hypervolemia (excessive blood volume), pulmonary edema, or other forms of heart failure.

Blood pressure can be measured in the pulmonary circulatory system with either the pulmonary artery pressure (PAP) or the pulmonary artery wedge pressure (PAWP). PAWP was difficult to measure before the introduction of the flow-directed, balloon-tipped catheter. This device has made catheter placement quicker, more effective, and safer, without the need for routine fluoroscopy. PAWP is closely related to the left atrial pressure and left ventricular end diastolic pressure. Increased PAWP has proved to be one of the earliest indications of left heart failure. Mean PAWP is normally about 5-12 mm Hg, but it may rise significantly with heart failure. PAWP measurements are also used to determine optimal cardiac output, and serve as guidelines for administering fluids and diuretics to control intravascular volume and drugs that increase the contractility of the heart thereby decreasing the work of the heart.

Pressure transducers are most commonly used for blood pressure monitoring, but they can also be used to measure intracranial, intrauterine, urinary bladder, and esophageal pressures and other selected pressures. To measure intracranial pressure (ICP), a small fluid-filled catheter may be introduced into the subdural or epidural space or into the ventricles of the brain for ICP transmission to an external transducer. Intracranial pressure is slightly pulsatile and can vary from a normal of 10 to 80 mm Hg. Excessive arterial $CO_2$ concentration, high arterial blood pressure, trauma to the head, and certain drugs can elevate ICP. High ICP levels that persist for more than a few minutes can cause cerebral dysfunction or brain death. Monitoring ICP permits immediate recognition of potentially dangerous levels and shows the effects of drugs or other means of reducing ICP to normal levels.

Uterine contractions during labor and delivery are sometimes monitored by direct intrauterine pressure (IUP) measurements. A long, fluid-filled catheter is introduced into the uterus and connected to a pressure transducer. IUP monitoring serves to measure the effect of oxytocin during the induction of labor. When labor has begun, changes in the IUP during uterine contractions may be recorded along with the fetal heart rate for the early detection of fetal distress.

Pressure measurements within the urinary bladder during urination are sometimes helpful in evaluating certain diseases of the bladder and urethra. Similarly, pressure measurements are sometimes used in diagnosing diseases involving the esophagus. With one or more balloons positioned in the esophagus, pressures within the balloon(s) are measured as the patient swallows. Esophageal pressure measurements may also be made to determine the effects of respiration on PAWP.

Physiologic pressure transducers have been reusable devices. The electrical elements used in reusable transducers are strain-sensitive resistive wires or semiconductor elements that are bonded to the diaphragm. A capacitor or inductor can be used instead of resistive elements to measure the displacement of the diaphragm. Resistive elements are connected with other resistors to form a Wheatstone bridge circuit. When an excitation voltage is applied across the bridge, the voltage output of the bridge is proportional to the displacement of the diaphragm.

Disposable transducers have several advantages over traditional reusable units. By using disposables, hospitals can stock many units and always have enough transducers to meet demands of the monitors available. The time and economic losses associated with repairing and replacing lost reusable transducers, especially miniature ones (accidental loss of transducers in dirty linen is not uncommon) is eliminated. A patient can be moved from one hospital area to another without the need to change transducers and/or monitoring kits, or keep track of the location of the transducer. In addition, the user always has a new device that has not been subjected to the abuses (e.g., dropping, impacting diaphragm) that a reusable could be exposed to during prior use and reprocessing (cleaning and sterilization).

An electrical risk related to direct blood pressure monitoring exists when pressures are measured in or near the heart. A saline-filled blood pressure catheter provides a direct conductive pathway between monitoring equipment and the heart as a low electrical current could reach the heart causing microshock and ventricular fibrillation. Current could enter the catheter via the transducer if there were inadequate electrical isolation between energized elements of the transducer (or parts of the case that can be touched by personnel attending the patient) and the saline. Direct blood pressure measurements can often be made on patients undergoing electrosurgery; it is possible that some current from the ESU may pass through the transducer. The transducer should not be damaged by this current, nor subject to excessive drift due to heating effects.

A pressure monitoring system arrives in the medical profession's hands air-filled. It must be purged and filled with fluid (saline). In this filling process, air bubbles may be trapped and are compressible compromising the dynamic response of the system. Therefore, non-faithful waveform reproductions result. A flowpath that contains steps, discontinuities, or that is non-uniform may serve to capture small or large air bubbles. These bubbles are not only difficult and time consuming to remove, but if not completely removed, will affect the waveform fidelity.

The dynamic response of a pressure monitoring system is normally limited more by length of the catheter extension tubing, compliance and air bubbles in the fluid path than by the monitor or the transducer. Determining the dynamic response of the transducer alone will not demonstrate how well a given physiologic waveform will be reproduced. The dynamic response of the system and the indwelling catheter will only determine the error in reproducing the pressure waveform. The response should be sufficient to reproduce the value of the systolic and diastolic pressures to within 5% of the original waveform with no significant distortion.

SUMMARY OF THE DISCLOSURE

Micromachining and silicone production techniques allow an etched pressure diaphragm with diffused piezoresistors for measuring displacement. The transducer can be made quite small. Since the diaphragm and sensing elements are integral, there is reduction of offset pressure signals due to thermoelastic strain between sensing elements and the diaphragm. Zero-drift and inaccurate measurements are minimized. The silicon diaphragm is a nearly perfect elastic material (i.e., it exhibits very little "memory" or hysteresis). The high sensitivity of the sensor diaphragm permits miniaturization reducing the displacement volume and improving frequency response.

Circuitry for a disposable pressure transducer system is contained on a thick film resistor network that may be laser trimmed to remove offset voltages and to precisely set its sensitivity to the same level as that of most reusable transducers (5 microvolt output per volt excitation per mm Hg pressure). The laser trimming also sets the temperature compensation. Thick film technology is employed to minimize the circuit size of the impedance matching portion disposed within the housing beneath the transducer diaphragm.

For most disposable pressure transducers, the resistance of their bridge elements must be high enough to overcome self-heating effects, which causes erroneous measurements. High resistance can result in an output impedance sufficient to cause an error when used with some blood pressure monitors. The combination of a high-output-impedance transducer and a low-input-impedance monitor may load the transducer, resulting in improper transfer of the pressure signal from the transducer to the monitor and an incorrect pressure display. Each transducer includes its impedance circuitry or buffer.

Where an impedance load exists, active electronics have been used to buffer the impedance of the transducer so that it is compatible with the monitor. It has been a concern for users that the transducer be provided with the proper cable including buffering circuits for the type of monitor to which it is connected. Active electronic cables intended to compensate for the high output impedance of the transducer element are designed to remain connected to their respective monitors. The excitation voltage normally supplied by the monitor to the transducer is used to power the active electronic circuitry in these buffering circuits.

In addition to the care with which the transducer and monitor are matched to one another, it is also important that the transducer be physically rugged enough to withstand handling and use and still provide accurate, reliable and repeatable pressure measurements. As explained, a thin silicon chip is etched to provide the transducer. The positioning and mounting of this delicate chip is critical to the performance of the transducer during pressure measurement no matter how severe normal handling becomes. Consequently, the way in which the chip is mounted and is exposed for and associated with the saline column of fluid pressure measurement is critical to the accuracy and performance of the device.

In addition to the concern of shock hazard, there is also concern for over pressuring the transducer element thereby shifting its calibration or destroying its dielectric integrity. Some transducers require an additional port for flushing air bubbles from the system and for zeroing the transducer to atmospheric pressure prior to monitoring. The preferred structure is such that it is resistant to overpressure to a greater degree than any available transducer and is configured to minimize the difficulty of debubbling.

The preferred transducer is geometrically configured such that it may be easily used in the disposable fashion in combination with monitoring equipment and other equipment designed for both disposable and reusable transducers. In particular, the transducer of the present invention has a cylindrical tube which fits in-line with the administration set, flush device and the like by means of luer lock connections designed to be compatible with the particular apparatus required for access to the monitored pressure fluctuations of the patient. In the side of this connecting passage, and normal thereto is a pressure port in which lies the etched diaphragm of the transducer element. Overlying the transducer element is a potting gel which has a high dielectric constant and is designed to seal the transducer from direct contact with the saline fluid of the system whereby the corrosive effects and conductive effects of the fluid are insulated from the diaphram. The gelatinous dielectric acts as an insulating or isolating sealant to permit only pressure fluctuations to reach the transducer diaphragm. The gel is situated to form a part of the wall of the cylindrical flow path and, therefore, does not obstruct the ease of debubbling. The insulating, isolating, and supporting gel is specifically formulated for ease of potting, electrical isolation, good sealing qualities, stability in manufacturing and anti-photo sensitivity. With regard to the latter, the gel includes a colorant which prevents light from having an effect on the transducer.

Because of the geometry of the cylindrical flow path and its orientation relative to the administration set and the catheter, the system is easily debubbled. Over all, the structure is rugged and has the right relationship of housing strength for support to prevent problems of over pressure. Syringes used to flush bubbles from within transducer domes and pressure tubing, to draw blood samples from monitoring lines, and to introduce drugs can be misused to dislodge clots from arterial catheters.

The transducer diaphragm is adequately supported such that pressure fluctuations are the only stress to which it is capable of responding. The full surface of the diaphragm is exposed to the pressure fluctuations but is not subjected directly to impact received by the body and cover within which the transducer is carried. That is to say that, the diaphragm is shock mounted within the unit so that direct loadings on the outside will not be directly absorbed by the transducer diaphragm. Similarly, the laser trimmed compensation circuitry is fully suspended to eliminate the effects to impact upon that delicate ceramic micro circuit board. The electrical output from the diaphragm is connected to the laser trimmed compensation circuit supported in a compact cover just beneath the diaphragm thereby minimizing losses incurred and elongated connections between the diaphragm and the compensation circuitry. Signals from the diaphragm in response to pressure fluctuations are amplified, filtered, and suitably modified by the circuitry integral with the cover and body that carry the diaphragm. The output signal is impedance matched and is sent through an ambient air pressure compensating cable to the specifically designed matched connection from the computer and readout apparatus. That connection is unique in that it carries both electrical and air pressure whereby venting of the underside of the diaphragm is remote from the diaphram and matching circuitry housing.

DETAILED DESCRIPTION OF THE DRAWINGS

Figure 1:
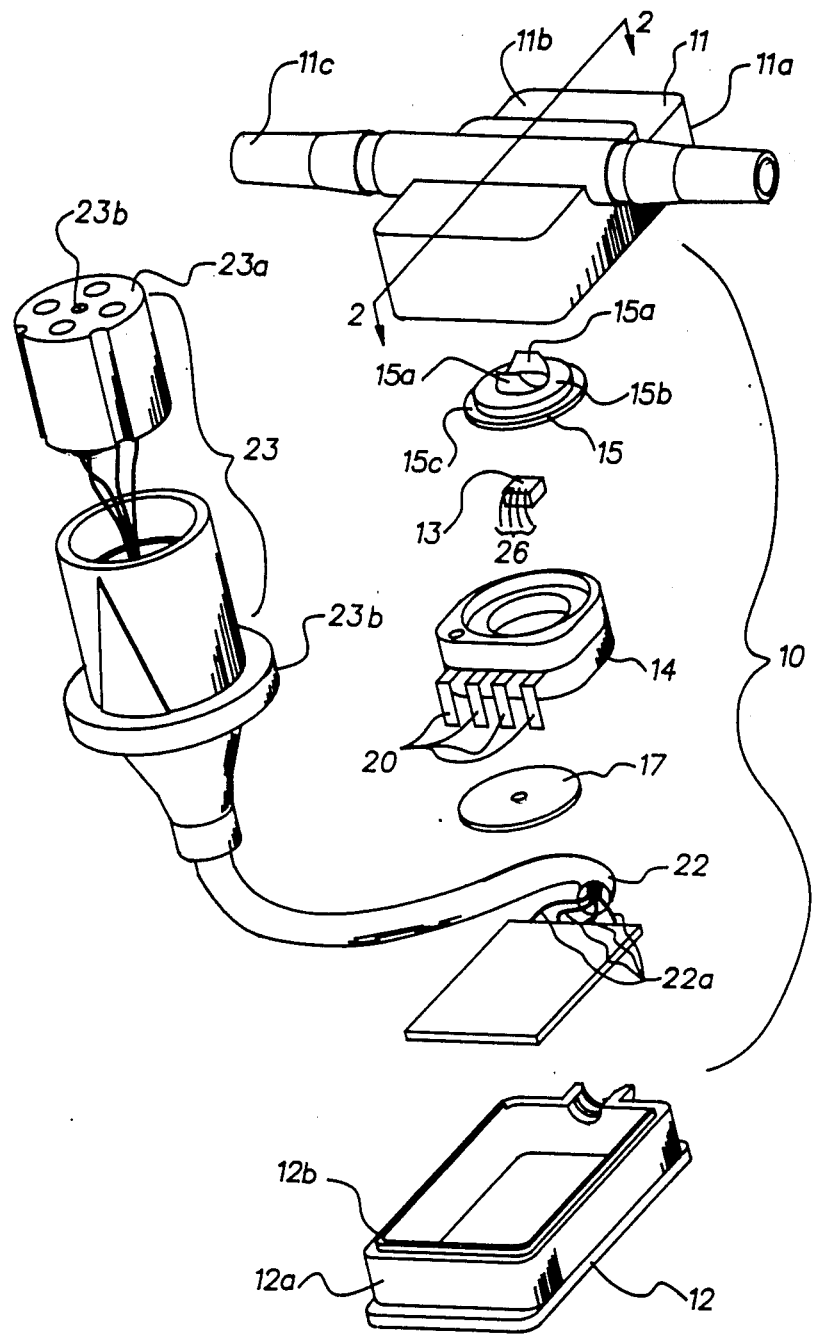
FIG. 1 is an exploded perspective view of the pressure transducer construction showing all of the relevant components of the preferred embodiment.

FIG. 1 shows an exploded perspective view of all of the components in the preferred embodiment and there is shown a housing 10 composed of a body 11 and a cover 12. The body 11 is a hollow rectangular case or open chamber with a wall 11a and a top 11b having a transverse tubular member 11c extending transversely across the top 11b of the body 11. Tubular member 11c encloses a cylindrical opening of circular cross section for matching with the connections to the administration set and the patient forming a uniform flow path. The cover 12 has a wall 12a which is configured to cooperatively engage with wall 11a on cover 11 by means of an upstanding flange 12b that extends thereabout around the top edge of the wall 12a. The flange 12b is positioned to fit just inside the wall 11a to form a lip type seal therebetween. Cover 12 is also hollow and caselike forming an open chamber and when cooperating with body 11 forms housing 10 an enclosure for the components of the transducer.

In a manner well known, the tubular member 11c can be connected to an administration set on one side and a catheter on the other whereby pressure pulses from the patient are hydraulically coupled via saline solution to interact with the transducer in the housing 10. More specifically, the transducer 13 is a thin semiconductor film resistive strain gauge element which is mounted within a support housing 14 in a manner which will expose the transducer to pressure fluctuations within the flow path through the tubular member 11c.

Figure 2:
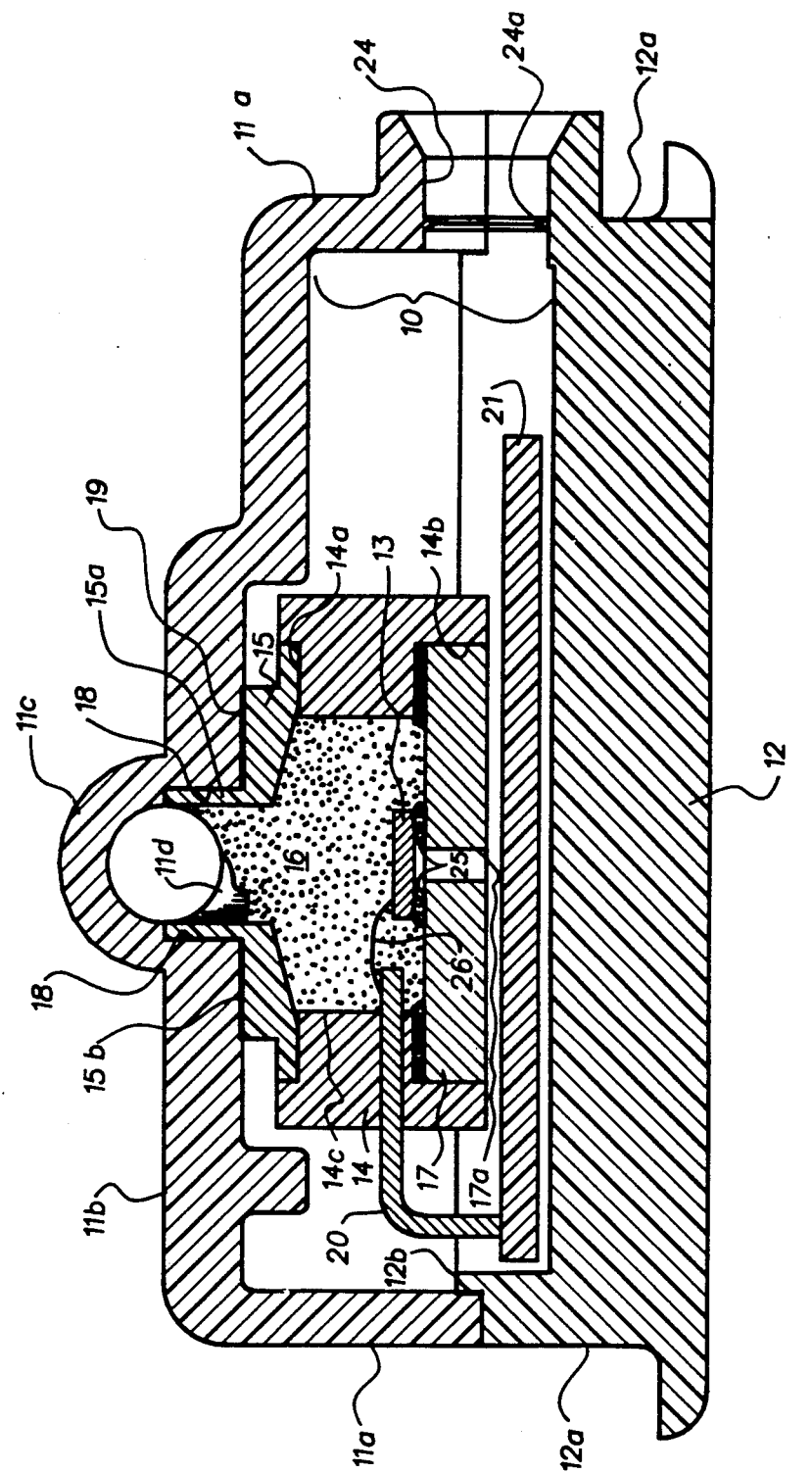
FIG. 2 is a cross-sectional view essentially along 2—2 of FIG. 1 showing the relative relationship of the transducer to the flow path and the mounting of same as well as the laser trimmed ceramic micro circuit board.

There is a coupling lid 15 which interconnects the tubular member 11c and the support housing 14. The relative relationship of the aforesaid components is best seen in FIG. 2 which is an enlarged side cross-sectional view (partially fragmented) of the complete assembly shown in exploded perspective in FIG. 1 as shown. The cross-section is taken essentially transverse to the tubular member 11c and through the middle of the housing 10.

The assembled cross-sectional view in FIG. 2 gives the relative relationship of the parts, and more clearly shows specific portions of the various components. In particular, there is the interrelationship between the upstanding flange 12b and the wall 11a which is shown assembled in FIG. 2. These components are bonded together at that juncture in the final assembly. In addition, the relative position of the body 11 and the coupling lid 15 are clearly disclosed, and the interrelationship of the flow path through the tubular member 11c and the transducer 13. In that regard, there is disposed between the flow path and the transducer 13 a pressure-responsive media 16 in the form of a silicone gel.

The location of the pressure responsive media 16 is defined by the internal hollow openings of the coupling lid 15 and the support housing 14. A sealing disk 17 forms the floor of the open hollow support housing 14. More particularly, and as shown in FIG. 2, the aforementioned assembled components and their stacked relationship form a hollow cavity the shape of which is the mold for the pressure responsive media 16. Starting with the cover 11, there is an opening 11d extending from the flow path of the tubular member 11c downwardly and into the hollow central portion of the housing 10. Opening 11d is generally circular in cross-section and slightly larger in one direction than the diameter of the flow path whereby recesses 18 exist and accept upwardly extending tangs 15a on coupling lid 15, thus forming a straight cylindrical hollow opening from the tangent point of the diameter of the flow path downwardly into the housing 10. See the partial fragmentary view of FIG. 2 which clearly shows the manner in which the tangs 15a arcuate to cooperate with the recesses 18 of opening and form a part of the flow path.

On coupling lid 15 and radiating outwardly from the tangs 15a is a top shoulder 15b which is adapted to be a mounting area against the inside of the top 11b of the cover 11. An adhesive layer 19 is positioned between the shoulder 15b and the inside of the top 11b such that lid 15 is adhesively secured to the cover. Lid 15 also includes a radiating rim 15c the outer periphery of which is essentially circular. Rim 15c conjugates within an upwardly open circular recess 14a of support housing 14 in mating engagement to center the housing 14 axially with respect to the cylindrical opening 11d of the cover 11. Therefore, components 11, 15, and 14 are all similarly aligned along a common axis (not shown). Support housing 14 also has a bottom circular recess 14b fashioned to accept therein the sealing disk 17.

Disposed between the recess 14a and the recess 14b is an inwardly extending web 14c composed of a thickened wall section in the center of the support housing 14. Consequently, the sealing disk 17 and the central bore 17a therein are coaxial with the support housing 14, the lid 15, and the cover 11. While coaxial alignment is not critical, it does provide a datum about which the hollow recess to be filled with pressure responsive media 16 is defined thus easing the filling of the hollow with the media 16.

The central bore 17a has a specific purpose in that the pressure transducer 13 is mounted thereabove such that air ambient air pressure can reach the bottom side of the pressure transducer 13. Consequently, pressure fluctuations transmitted through the pressure responsive in media 16 act upon one side of the transducer 13 and are measured against ambient air pressure on the other side thereof. The pressure transducer 13 is logically disposed immediately above the opening of central bore 17a. Sealing disk 17 is metallic such as aluminum and adhesively bonded and is a slight press fitted with interference with respect to recess 14b of support housing 14. The adhesive used in the preferred embodiment is known as RTV. While the final assembled position of the relative components can be seen in FIG. 2, there is a technique and method used to assemble them. Before explaining that particular procedure, various other components of the assembly ought to be described.

As can be seen in FIGS. 1 and 2, there are four buss bars 20 extending through one side of the wall of inwardly extending web 14c of support housing 14 and outwardly and downwardly therefrom. These buss bars 20 are molded into the support housing 14 and are made of highly conductive metal such as copper or phosphor bronze. Hanging in cantilever fashion off the downwardly extending buss bars 20 is a ceramic circuit board 21. Circuit board 21 in the preferred embodiment includes the following circuitry impedance matching, temperature compensation, and trimming network. The buss bars 20 offer support and electrical connection to the circuit board, which as shown in FIG. 1 is connected to a cable 22 by means of wires 22a. The cable 22 extends to an outlet connector 23 composed of a female socket 23a and a manipulative housing 23b. The wiring connections with respect to cable 22 and its wires 22a are not shown in FIG. 22, however, those skilled in the art will no doubt appreciate that the cable 22 is fitted through an opening 24 in the side of the housing 10 whereby, in a well-known manner, a strain relief is formed. In this particular circumstance, there is a rib 24a which circumscribes the inside of the opening 24 and provides a contact point a9ainst the outside sheath of cable 22. In order to further secure the combination, a mounting adhesive is applied between the juncture of the cable 22 and the opening 24, particularly in the area of the rib 24a.

As shown in FIG. 2, the transducer 13 is resiliently bonded to the sealing disk 17 by means of application of a resilient adhesive 25. The preferred technique for assembly of the pressure transducer starts with the transducer 13 and disk 17. The transducer is adhesively bonded at 25 to the sealing disk 17 and the combination is adhesively bonded into the support housing 14 and more particularly, the disk 17 being seated in recess 14b. Thereafter the transducer is connected to the buss bars 20 by connecting wires 26 shown in FIGS. 1 and 2. A small amount of pressure responsive media 16 is then applied to the hollow formed within the web 14c of support 14 to just fill the area defined by the coupling lid 15 whereby the assembly of the coupling lid 15 to the support housing 14 is accomplished. That is not to say that, the pressure response in media 16 is completely filled to form the concave circular bottom for the flow path through tubular member 11c. That procedure is followed at the point where the coupling lid 15 is just about ready to be assembled to the recesses 18 of the cover 11.

So it can be seen that the application of the pressure responsive media 16 is a two-step process, the latter step to form the concave circular bottom of the flow path through the tubular member of 11c. At that point, the package of lid 15 and support housing 14 are pressed up against the inside of body 11 with solvent 19 (methylene chloride) to form a bonded interface 19 being applied to the surface of shoulder 15b and the inside of top 11b to form a tight bond therebetween. As shown in FIG. 1, the tangs 15a are aligned for forming the uniform circular flow path through the tubular member 11c of the body 11. The cable 22 and its connecting wires 22a are then connected to the microchip 21 carried on the buss bar 20 such that same is suspended as shown in FIG. 2. The cable 22 is laid into the opening 24 and against the strain relief rib 24a of the body 11. The cover 12a is then bonded by means of adhesive applied along the juncture between the upstanding flange 12b and the inside wall 11a of the body 11. Some more adhesive is placed on the juncture between the cable 22 and the opening 24 and the package is tightly conjugated to form a sealed package having enclosure 10. In the cable 22 is an air passage 23b shown in FIG. 1 which equalizes the air pressure inside the housing 10 with that of the ambient. The cable connects with another (not shown) and extends to a computer which is designed to receive, analyze and record the signals from the transducer.

Those skilled in the art will appreciate that a suspended shock mounting has been formed for not only the pressure transducer 13 but also the ceramic laser trimmed micro circuit 21. In particular, the transducer 13 is resiliently bonded by means of adhesive 25 to the sealing disk 17 which is also resiliently bonded to the inside of recess 14b of the support housing 14. The latter being carried in depending fashion from the coupling lid 15 which is adhesively secured to the inside of the body 11. Any impact imposed upon the cover 12 or the body 11 has no direct connection with either the pressure transducer or the ceramic microcircuit 21 because of the adhesive bonding and the cantilever mounting of buss bars 20. It should be appreciated that the concept sought to be protected in the claims which follow covers the shock mounting as well as the uniform circular flow path, the former giving the product its ruggedness and the latter making same easy to debubble. Therefore, alterations in the basic geometry or configurations, materials used or techniques for fabrication are within the scope of the claims.

What is claimed:
1. A pressure transducer assembly for monitoring pressure in a fluid comprising:
 a hollow body having an open chamber and a uniformly dimensioned passage defining a flow path with an inlet and outlet port in fluid flow communication with said flow path and an opening in said flow path extending to said chamber,
 a mounting means being an electrical insulator and having a centrally opened web with a receiving well extending outwardly therefrom and a trans- ducer supporting portion in communication therewith, a lid means having a first area shaped to close a part of said opening and maintain a section of said uniformly dimensioned passage and a second area configured to fit within said mounting means receiving well and said first and second areas having a passageway extending therethrough to connect said flow path to the area of said opened web, a pressure transducer means secured in said supporting portion and exposed to said central opening of said web and said lid means passageway for determining and converting fluid pressure in said flow path into electrical signals, a fluid pressure responsive media which is electrically non-conductive said media closing the rest of said opening and filling said passageway between said flow path and said transducer, an electrical conducting means connected to said pressure transducer means and extending through said web and out of said mounted means as electrical connection lugs; and integrated circuit means mounted to said lugs and connected to an output cable for modifying the signal from said transducer means to permit the signal to be read directly on a measuring instrument.

2. The pressure transducer assembly of claim 1 wherein said fluid pressure responsive media in said opening being shaped to conform to the wall of said flow path for forming a uniform flow path cross section between said inlet port and said outlet port.

3. The pressure transducer assembly of claim 1 wherein said flow path is comprised of a tube having sidewalls and openings connected between said inlet and outlet ports and said opening is cylindrical and normal to the path of flow and said lid means has upstanding arcuate portions thereon which conformed to the side walls of said tube at the side openings thereof upon placement of same therewithin and in combination with said pressure responsive media form a smooth tubular flow path of uniform cross section from said inlet to said outlet ports.

4. The pressure transducer assembly of claim 1 wherein said lid means is sealed within said receiving well and is sealed to said opening in said flow path for fluid communication between said flow path and said transducer means.

5. The pressure transducer assembly of claim 1 wherein said pressure transducer means is resiliently connected to said centrally opened web.

6. The pressure transducer assembly of claim 1 wherein said integrated circuit means includes signal modifying means for appropriately setting impedance from said transducer to the instrument for analyzing and recording the information transduced.

7. The pressure transducer assembly of claim 1 wherein a hollow cover is provided and shaped to seal said body and form an enclosure.

8. The pressure transducer assembly of claim 7 wherein said outlet cable is cooperatively engaged by said body and said cover to form a strain relief.

9. A pressure transducer assembly for monitoring pressure in a fluid comprising:

a hollow body having an open chamber and a uniformly dimensioned passage defining a flow path with an inlet and outlet port in fluid flow communication with said flow path and an opening in said flow path extending to said chamber, a connecting means for support being an electrical insulator and having first and second sides with a central opening therethrough and said first side being bonded to said flow path opening, a pressure transducer means resiliently secured to said second side and exposed to said central opening of said connecting means for determining and converting fluid pressure in said flow path into electrical signals, a fluid pressure responsive media which is electrically non-conductive filling said central opening between said flow path and said transducer means, an electrical conducting means connected to said pressure transducer means and extending through said connecting means and out thereof forming as electrical connection lugs, integrated circuit means mounted to and supported by said lugs at one end and connected to an output cable at the other end for modifying the signal from said transducer means to permit the signal to be read directly on a measuring instrument; and cover means sealing said body chamber and forming an enclosure and cooperating therewith as a strain relief for said output cable so the connection therefrom to said integrated circuit cannot impose a load thereon.

10. The pressure transducer assembly of claim 9 wherein said pressure transducer means is resiliently secured to said second side by said fluid pressure responsive means.

11. The pressure transducer assembly of claim 10 wherein said second side includes a recess supporting and protecting said transducer means resiliently secured therein and said central opening has a peripheral flange thereabout for providing a mounting place for said resiliently secured pressure transducer means.

12. The pressure transducer assembly of claim 9 wherein said connecting means for support includes a portion thereon which fits within said flow path opening to provide a uniform cross sectional area from said inlet to said outlet ports when said fluid pressure responsive media is filled within the opening in said connecting means.

13. The pressure transducer assembly of claim 9 wherein said a cover means is hollow and open forming its own chamber and includes an upstanding flange shaped to seal with said body.

14. The pressure transducer assembly of claim 13 wherein said outlet cable is cooperatively engaged by said body and said cover means thereby forming a strain relief.

15. The pressure transducer assembly of claim 13 wherein said connecting means depends from said hollow body and said pressure transducer is resiliently carried by said connecting means and said integrated circuit means is connected to said electrical conducting means and is carried cantilever fashion by said connecting means within the enclosure formed by said body and where said cover means and the inside surface of said cover means does not in any way interfere with or engage any portion of said integrated circuit means or connecting means such that said pressure transducer is resiliently suspended from said connecting means without carrying any stresses from said hollow body or said cover means.

* * * * *